United States Patent [19]

Yannopoulos

[11] 4,382,974

[45] May 10, 1983

[54] SYNTHETIC MONAZITE COATED NUCLEAR WASTE CONTAINING GLASS

[75] Inventor: Lympexios N. Yannopoulos, Churchill, Pa.

[73] Assignee: Westinghouse Electric Corp., Pittsburgh, Pa.

[21] Appl. No.: 245,488

[22] Filed: Mar. 19, 1981

[51] Int. Cl.[3] .......... A61N 5/12
[52] U.S. Cl. .......... 427/5; 252/629
[58] Field of Search .......... 252/629; 427/6, 5

[56] References Cited

PUBLICATIONS

"Material Research Bulletin", New York, vol. 13 (11) 1978, pp. 1239-1245, McCarty et al.
DOE/ET/41900-T2, 5/15/80, pp. 2-4, 21, 24.
DOE/ET/41900-1, pp. 3, 15.
Science, vol. 204, Apr. 20, 1979, pp. 289-291.

*Primary Examiner*—Sam Silverberg
*Attorney, Agent, or Firm*—R. D. Fuerle

[57] ABSTRACT

A method is disclosed for stabilizing glass which contains nuclear waste by coating the glass with synthetic monazite. The synthetic monazite has a composition of about 30 to about 35% $Ce_2O_3$, about 31 to about 36% $La_2O_3$, about 27 to about 35% $P_2O_5$, and about 2 to about 5% $Nd_2O_3$, where the percentage of $La_2O_3$ is about 0.5 to about 1.5 percentage points greater than the percentage of $Ce_2O_3$. The coating can be applied by detonation gun or by chemical vapor deposition. Chemical vapor deposition can be accomplished by heating halides of La, Ce, Nd, and P or PO and bringing the vapors by carrier gas to the glass where they are contacted by an oxidizing gas such as carbon dioxide, oxygen, steam, or air.

12 Claims, 1 Drawing Figure

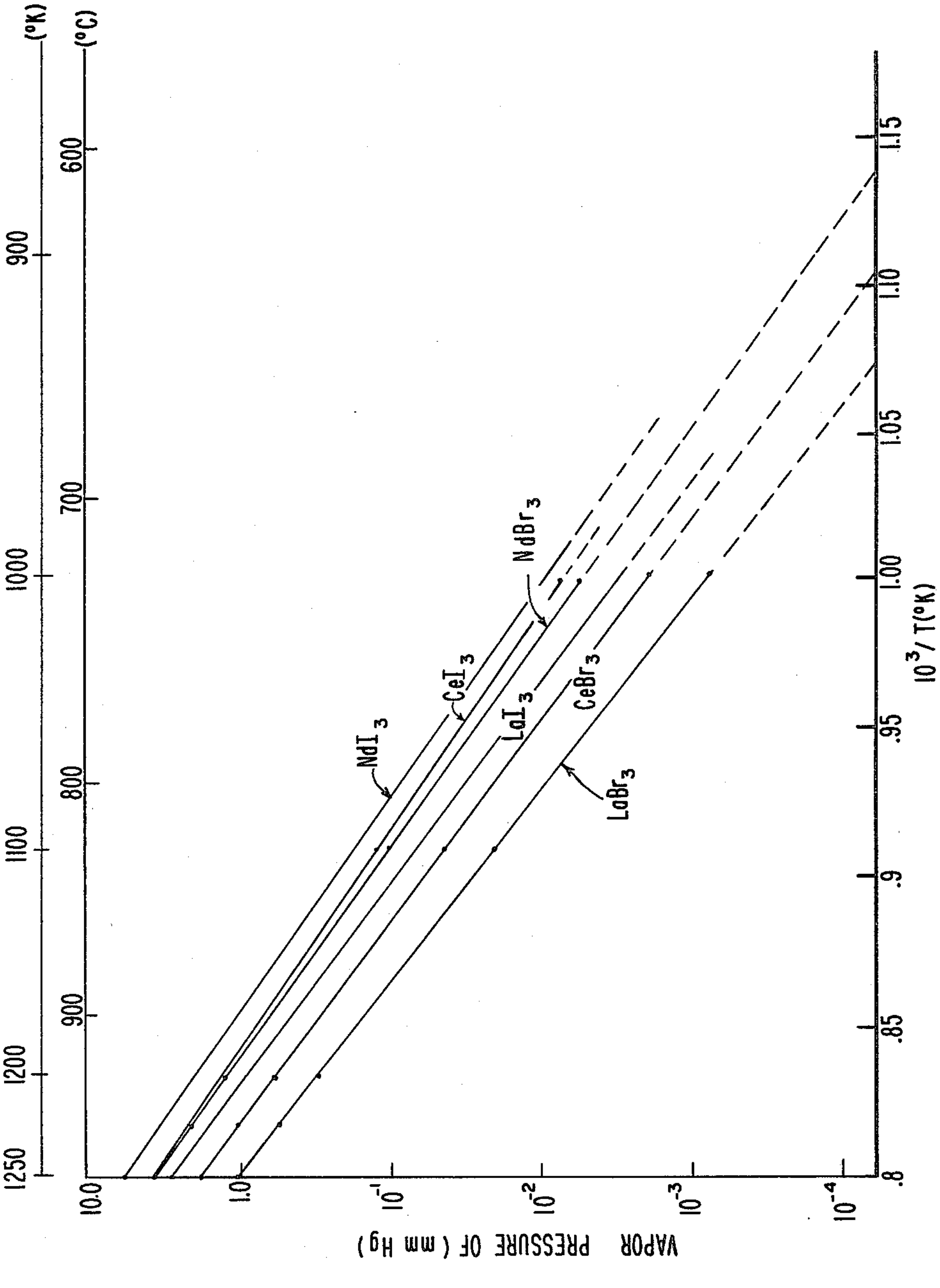
(°K)
(°C)
NdI3
CeI3
LaI3
CeBr3
LaBr3
NdBr3
VAPOR PRESSURE OF (mm Hg)
10³/T(°K)

SYNTHETIC MONAZITE COATED NUCLEAR WASTE CONTAINING GLASS

BACKGROUND OF THE INVENTION

The single biggest roadblock to the growth of commercial nuclear power in the United States is the resolution of the problem of nuclear waste storage or disposal. Until it can be demonstrated that nuclear waste can be stored safely, growth of the nuclear industry in this country will be seriously retarded. At the present time the general procedure for disposal of nuclear waste from commercial reactors, defense processes, and other sources is to first convert them into an alkaline solution. The liquid is then heated and evaporated to convert the waste into a powder called calcine. The calcine is mixed with borosilicate glass frit and is heated to melt the glass, either in the container in which it is to be stored or in a furnace from which it is poured into a storage container.

Due to corrosion problems with the glass produced by this process, an alternative process known as the cermet process, has also been developed. In the cermet process an iron nickel base metal matrix contains the fission product oxides from the high level waste. The cermet produced by this process is a continuous electrically conductive metal matrix containing small particles (about 1 micron) of waste oxide. The process is described more fully in U.S. Pat. No. 4,072,501. The final sintered waste cermet articles produced by this process could be in the form of pellets or rods. Currently cylindrical pellets 0.6 inches in diameter and 0.6 inches long are conveniently extruded.

Another process under consideration which avoids the high temperatures required in the borosilicate glass and cermet processes is to contain nuclear wastes in glass produced by the low temperature polymerization of metal alkoxides. These processes are described in U.S. Pat. application Ser. No. 162,967, filed June 25, 1980; U.S. Pat. application Ser. No. 176,738, filed Aug. 11, 1980; and U.S. Pat. application Ser. No. 162,966, filed June 25, 1980.

The product of all of these processes is a type of glass which contains the nuclear waste. The stability of the product depends on its ability to resist leaching or corrosive processes. Leach data for borosilicate glasses, for example, indicates that the glasses are not sufficiently resistant to leaching to provide long-term stability (i.e., greater than 500 years). Thus the alteration of these glasses is necessary before they can be safely used for the storage of nuclear waste.

SUMMARY OF THE INVENTION

I have discovered that glass containing nuclear waste can be stabilized by coating the glass with a layer of synthetic monazite. The stability of the glass can be further increased by the addition of small amounts of synthetic monazite to the glass composition during its formation. The stabilized nuclear waste-containing glass products of this invention are expected to be able to resist leaching and weathering for a period of time far in excess of that necessary to insure the safe storage of nuclear waste materials.

I have also found that the components of synthetic monazite can be deposited by chemical vapor deposition.

PRIOR ART

An article by M. M. Abraham et al., titled "Preparation and Compaction of Synthetic Monazite Powders," in Radioactive Waste Management, Volumes 1 (2), September 1980, pages 181 to 191, discloses the formation of a synthetic monazite composition containing nuclear wastes.

An article by Q. H. Leonardos, Jr., in Economic Geology, Vol. 69, p. 1126 (1974) states that natural monazite crystals have survived $10^9$ years of weathering from both granite and quartzite along with other metamorphic geological processes, and now occur on beach sands.

An article by Yasuo Hikichi, Ken-iti Hukuo and Jiro Shiokawa in the Bulletin of the Chemical Society of Japn, Vol. 51 (12), 3645-3646 (1978), describes the preparation of synthetic monazite.

DESCRIPTION OF THE INVENTION

The accompanying FIGURE is a graph which gives the vapor pressures of $LaBr_3$, $CeBr_3$, $NdBr_3$, $LaI_3$, $CeI_3$, and $NdI_3$ at various temperatures.

In this invention glass which contains nuclear waste is coated with synthetic monazite. The synthetic monazite of this invention differs from the natural monazites in that the latter contain larger amounts of tetravalent ions such as thorium and uranium in their predominantly trivalent system. The tetravalent substitutions are accompanied by a charge balancing substitution of divalent ions such as calcium and lead. This ability to accommodate such chemically diverse cations may be due largely to the irregular coordination around the metal ions which, from the standpoint of crystal symmetry, does not place severe constraints on the cations. The absence of the transuranium elements from synthetic monazite as well as the divalent ions such as calcium and lead mean that the synthetic monazite is expected to trap the tetravalent transuranium elements which diffuse from the glass and prevent their escape into the environment. The synthetic monazite has the general formula $(Ce,Lu,Nd)PO_4$. Its specific formula would be $(Ce_{0.486}La_{0.476}Nd_{0.038})PO_4$. Its composition expressed as a weight percent of its component-oxides would be $Ce_2O_3$ 33.0%, $La_2O_3$ 34.0%, $Nd_2O_3$ 2.7%, $P_2O_5$ 29.3%. However, suitable synthetic monazite compositions can be made within the range of about 30 to about 35% $Ce_2O_3$, about 31 to about 36% $La_2O_3$, about 27 to about 35% $P_2O_5$ and about 2 to about 5% $Nd_2O_3$. The percentage of $La_2O_3$ should be about 0.5 to about 1.5 percentage points greater than the percentage of $Ce_2O_3$ to maintain the proper proportion of the two elements.

The glass treated by this invention may be borosilicate glass, aluminum silicate glass, or any other type of glass, including calcine and cermet. The glass may have almost any shape or size and still be treated successfully with the technique of this invention.

Synthetic monazite can be coated on the glass by a variety of techniques, but chemical vapor deposition and detonation gun are the two preferred techniques. In chemical vapor deposition a stoichiometric amount of the halides of the elements necessary to form the synthetic monazite are vaporized, then oxidized and deposited as monazite on the glass within a furnace, preferably a temperature gradient furnace. The halides which are used in the chemical vapor deposition are $LaX_3$, $CeX_3$, $NdX_3$, and $PX_3$ or $POX_3$ or a mixture of $PX_3$ and $POX_3$. In order to deposit the oxides in the correct proportions it is necessary to heat each halide to a temperature such that the resulting halide vapor pressures are in the same proportion as the metal oxides in the monazite deposit. However, $PoX_3$ or $PX_3$ can be used in excess of stoichiometric; they are preferably used by doping the carrier gas with about 0.5 to about 1% $POX_3$ or $PX_3$. The X in these formulae can be bromine, iodine, or chlorine, but is preferably bromine as the bromides, unlike the iodides, do not attack the quartz tube often used as the reaction chamber in the furnace.

The temperature necessary to achieve a particular vapor pressure of a lanthanum, cerium, or neodymium halide, where the halide is a bromide or an iodide, can be determined from the accompanying drawing. For example, vapors in the proper proportion may be obtained if cerium bromide is heated to 850° C. which produces a vapor pressure of $8.5\times10^{-2}$ millimeters of mercury, lanthanum bromide is heated to 876° C. with produces a vapor pressure of $8.32\times10^{-2}$ millimeters of mercury and neodymium bromide is heated to 609° C. which produces a vapor pressure of $6.60\times10^{-5}$ millimeters of mercury. Using iodides, vapor pressures in the proper proportion can be obtained if cerium iodide is heated to 850° C. which produces a vapor pressure of $2.300\times10^{-1}$ millimeters of mercury, lanthanum iodide is heated to 870° C. which produces a vapor pressure of $2.225\times10^{-1}$ millimeters of mercury, and neodymium iodide is heated to 675° C. which produces a vapor pressure of $1.745\times10^{-3}$ millimeters of mercury.

A carrier gas is needed to carry the halide vapors to the nuclear waste containing glass. The carrier gas is preferably nitrogen but other inert gases could also be used. The carrier gas is typically used at a flow rate of about 0.1 to about 0.3 liters a minute.

An oxidizing gas such as $CO_2$, steam, oxygen, or air is needed to convert the halides into the oxides. For example, carbon dioxide would oxidize lanthanum halide according to the following equation.

$$LaX_3+POBr_3+3CO_2\rightarrow LaPO_4+3Br_2+3CO$$

The preferred oxidizing gas is oxygen or air as those gases do not produce carbon monoxide as carbon dioxide does. The flow rate of the oxidizing gas should be about 0.1 to about 0.3 liters per minute.

The oxidizing gas should be admitted to the chemical vapor deposition chamber at a point near the radioactive waste containing glass so that the halides are not oxidized until they are nearly in contact with the glass. The glass should be heated below its softening point, typically about 800° C., and should be rotated or mixed to insure coating on all sides. The chemical vapor deposition process should continue until a coating about 200 to about 500 microns has been built up on the glass as thinner coatings may be porous and thicker coatings are unnecessary.

In the detonation gun coating process hot particles of monazite are impinged at high velocity into the glass material, which can be at room temperature. The detonation gun produces supersonic velocities on the order of about 2,500 ft./sec. which produce a bond strength between the monazite coating and the glass in excess of 25,000 psi. The detonation gun method provides reproductible coatings due to the precise control that is obtained over the process variables. The recommended typical coating thickness using the detonation gun coating process are about 200 to about 250 microns.

The synthetic monazite used in the detonation gun coating process can be produced by coprecipitation from aqueous solutions of mixtures of the corresponding nitrates of the lanthanides by the addition of a solution of ammonium dihydrogen phosphate. The starting materials are the lanthanide oxides ($La_2O_3$, $Ce_2O_3$, and $Nd_2O_3$) of purity 99.95–99.99% which are mixed with dilute (18%) nitric acid and "pure" grade $NH_4H_2PO_4$. The resulting precipitate is heated to about 1,000° in air for about 2 hours to obtain the anhydrous monoclinic monazite structure. Precipitation can be better controlled to yield a well-filtered product by using urea to slowly raise the pH of the solution. The latter is added in granular form and the mixture is heated at 180° C. until precipitation occurs. The precipitate is preferably preheated at 400° C. before the final calcination step for the conversion to the monoclinic monazite. Further details of the preparation of synthetic monazite can be obtained from an article by I. A. Bondar, A. I. Domensky and L. P. Menzensen in the Russian Journal of Inorganic Chemistry, Vol. 21, 8, p. 1126 (1976) and from the book, "Precipitation From Homogeneous Solution," by L. Gordon, M. L. Satusky, and H. Willard, published by John Wiley & Sons in 1959, both herein incorporated by reference.

The nuclear waste containing glasses can be further stabilized by the addition of about 2 to about 5% of synthetic monazite to their compositions prior to their preparation. The resulting glasses may be coated with synthetic monazite, if desired, to further enhance their stability.

I claim:

1. A method of stabilizing glass containing nuclear waste comprising applying to said glass by either chemical vapor deposition or using a detonation gun a coating consisting essentially of synthetic monazite.

2. A method according to claim 1 wherein said monazite has a composition which comprises about 30 to about 35% by weight $Ce_2O_3$, about 31 to about 36% by weight $La_2O_3$, about 27 to about 35% by weight $P_2O_5$, and about 2 to about 5% by weight $Nd_2O_3$, where the percentage of $La_2O_3$ is about 0.5 to about 1.5% greater than the percentage of $Ce_2O_3$.

3. A method according to claim 2 wherein said monazite comprises about 33% by weight $Ce_2O_3$, about 34% by weight $La_2O_3$, about 29.3% by weight $P_2O_5$, and about 2.5% by weight $Nd_2O_3$.

4. A method according to claim 1 including the step of adding about 2 to about 5% by weight of synthetic monazite to the composition from which said glass is formed.

5. A method according to claim 1 wherein said coating is about 200 to about 500 $\mu m$ in thickness.

6. A method according to claim 1 wherein vapors of $LaX_3$, $CeX_3$, $NdX_3$, and $PX_3$ or $POX_3$ are brought by carrier gas to said glass where they are contacted by an oxidizing gas, where each X is independently selected from chlorine bromine, and iodine.

7. A method according to claim 6 wherein X is bromine.

8. A method according to claim 6 wherein said carrier gas is nitrogen and said oxidizing gas is carbon dioxide, oxygen, steam, or air.

9. A method according to claim 6 wherein said $POX_3$ or $PX_3$ constitutes about 0.5 to about 1% of said carrier gas.

10. A method according to claim 6 wherein said carrier gas and said oxidizing gas flow past said glass at about 0.1 to about 0.3 l/min.

11. A method according to claim 1 wherein said glass is coated using a detonation gun.

12. A method according to claim 1 wherein said coating is made by chemical vapor deposition.

* * * * *